(12) United States Patent
Bergeron

(10) Patent No.: US 6,648,910 B1
(45) Date of Patent: *Nov. 18, 2003

(54) SYSTEM FOR THREE-DIMENSIONAL POSITIONING OF INSTRUMENTS BY INTRALUMINAL TRACT

(76) Inventor: Patrice Bergeron, 38, boulevard Lei-Roure, F-13009 Marseille (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/485,878
(22) PCT Filed: Jun. 25, 1999
(86) PCT No.: PCT/FR99/01537
§ 371 (c)(1), (2), (4) Date: May 25, 2000
(87) PCT Pub. No.: WO99/66861
PCT Pub. Date: Dec. 29, 1999

(30) Foreign Application Priority Data

Jun. 25, 1998 (FR) .............................. 98 08092

(51) Int. Cl.$^7$ .................................................. A61F 2/06
(52) U.S. Cl. ..................................................... 623/1.11
(58) Field of Search ........................... 623/1.11–2, 23.7; 606/191, 194, 195

(56) References Cited

U.S. PATENT DOCUMENTS

| | | | | | |
|---|---|---|---|---|---|
| 5,613,980 | A | * | 3/1997 | Chauhan | 128/898 |
| 5,720,735 | A | * | 2/1998 | Dorros | 604/284 |
| 6,093,203 | A | * | 7/2000 | Uflacker | 623/1.12 |
| 6,096,073 | A | * | 8/2000 | Webster et al. | 623/1.16 |
| 6,183,509 | B1 | * | 2/2001 | Dibie | 623/1.35 |

* cited by examiner

Primary Examiner—Michael J. Milano
Assistant Examiner—(Jackie) Tan-Uyen Thi Ho
(74) Attorney, Agent, or Firm—Piper Rudnick LLP

(57) ABSTRACT

The invention concerns a device for positioning an instrument introduced in the arterial system by endoscopic process, consisting of a tubular element with an asymmetrical lateral extension for angular positioning of the instrument.

10 Claims, 4 Drawing Sheets

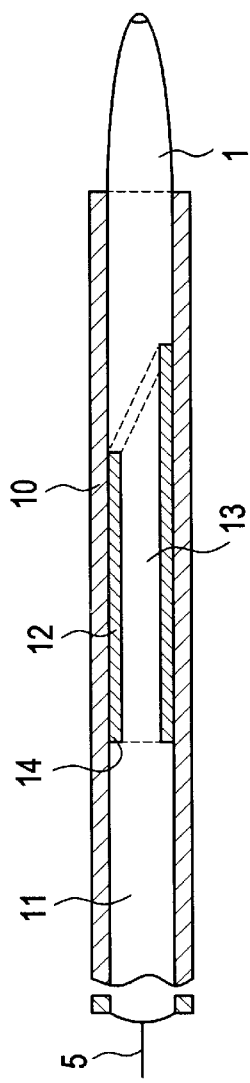
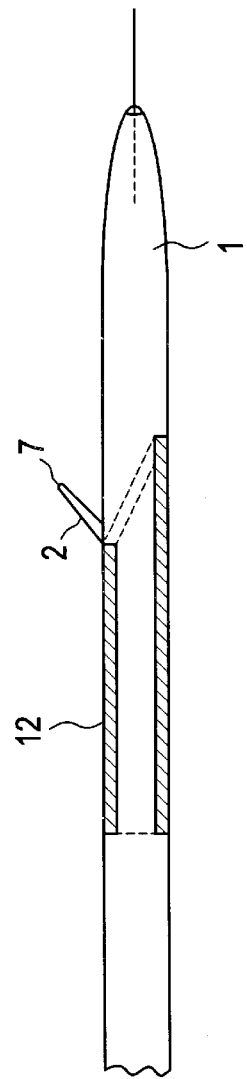
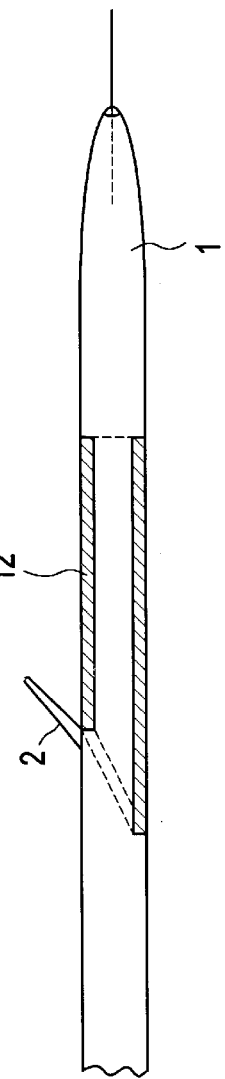

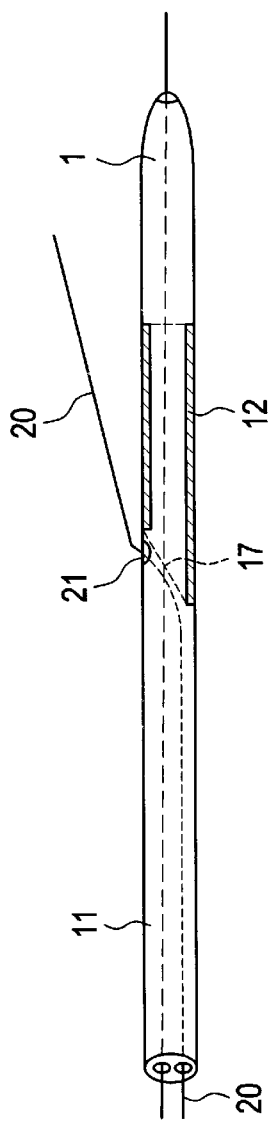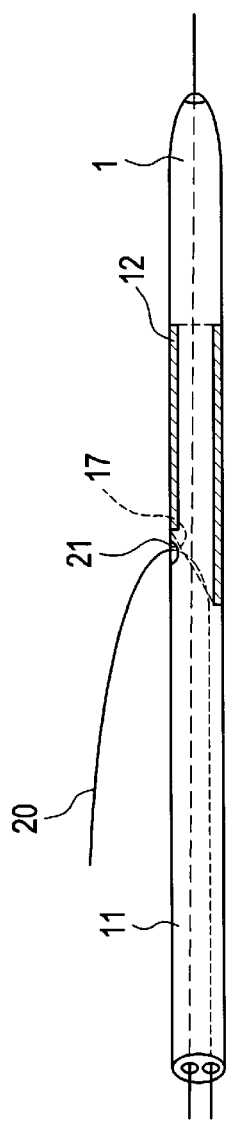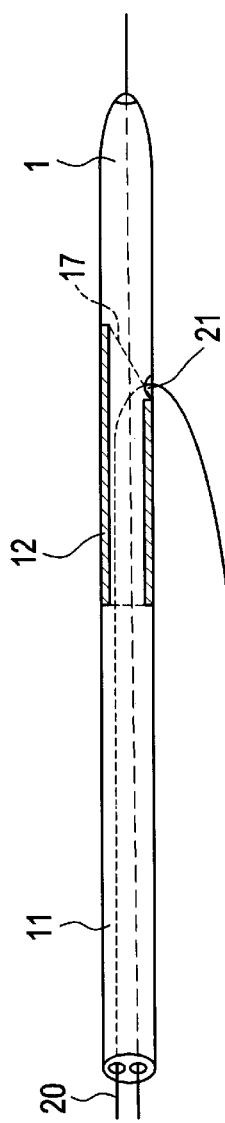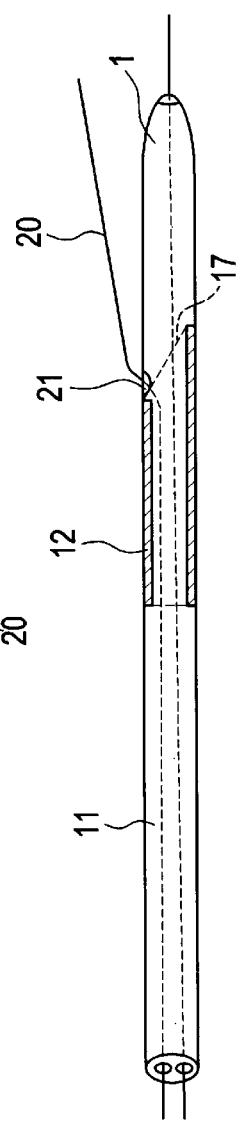

SYSTEM FOR THREE-DIMENSIONAL POSITIONING OF INSTRUMENTS BY INTRALUMINAL TRACT

FIELD OF THE INVENTION

The present invention pertains to the field of angioplasty.

More specifically, the invention pertains to a device designed for the introduction of an apparatus, for example, a stent, into the arterial network via the endoscopic route.

BACKGROUND

The invention has the goal of resolving the problem of positioning an apparatus such as a beveled stent at the level of a bifurcation. The beveled stent has a slant which must be positioned angularly so as to optimize blood circulation.

Known in the state of the art are various solutions for positioning beveled stents. As an example, patent application PCT/US97/18201 describes a beveled stent and apparatus constituted by a balloon guided by a guide thread. A stabilization catheter guided by a second guide thread is designed to prepare the positioning of a bifurcation. These are two independent means such that it is not possible to position in a simple and effective manner the instrument for introduction of the beveled stent, nor to assure in an ergonomic manner the angular positioning of the stent introduction element in the lateral branch.

Another patent, published as EP891751, discloses a balloon comprising a coil which comes to be positioned in the principal artery so as to facilitate the positioning of a balloon in a lateral branch.

SUMMARY OF THE INVENTION

The invention pertains to a device for positioning an apparatus introduced into the arterial network via the endoscopic route, characterized in that it is constitutecd by a tubular element presenting an asymmetrical lateral extension for the angular positioning of the apparatus.

This asymmetrical extension enables an angular positioning of the device in relation to the orientation of the bifurcation.

According to a first mode of implementation, the tubular element is constituted by an inflatable balloon.

Advantageously, the tubular element is formed by an inflatable balloon extended by a lateral protuberance.

According to a second mode of implementation, the tubular element is extended by a lateral projection for the angular positioning of the apparatus.

According to a preferred variant, the lateral extension presents a radio-contrasted reference point.

According to another advantageous variant, the device comprises a retention means for maintaining the lateral extension in a folded down position against the tubular element during the introduction phase.

According to an implementation example, the retention means is constituted by a connection that can be released by pulling on a thread.

According to an implementation variation, the positioning device has a detachable sleeve which, at the time of introduction into the artery, surrounds the stent and the lateral protuberance, in a manner such that the sleeve can be withdrawn close to the bifurcation so as to release the lateral extension.

Preferably, the detachable sleeve has an asymmetrical radio-opaque marker.

BRIEF DESCRIPTION OF THE DRAWINGS

Better comprehension of the invention will be provided by the text below with reference to a nonlimitative example of implementation in which:

FIG. 3 shows a sectional view of an implementation variant,

FIGS. 4 and 5 show views of implementation variants after removal of the detachable sleeve, FIGS. 6 to 9 show other implementation variants.

DETAILED DESCRIPTION

Figure 1:
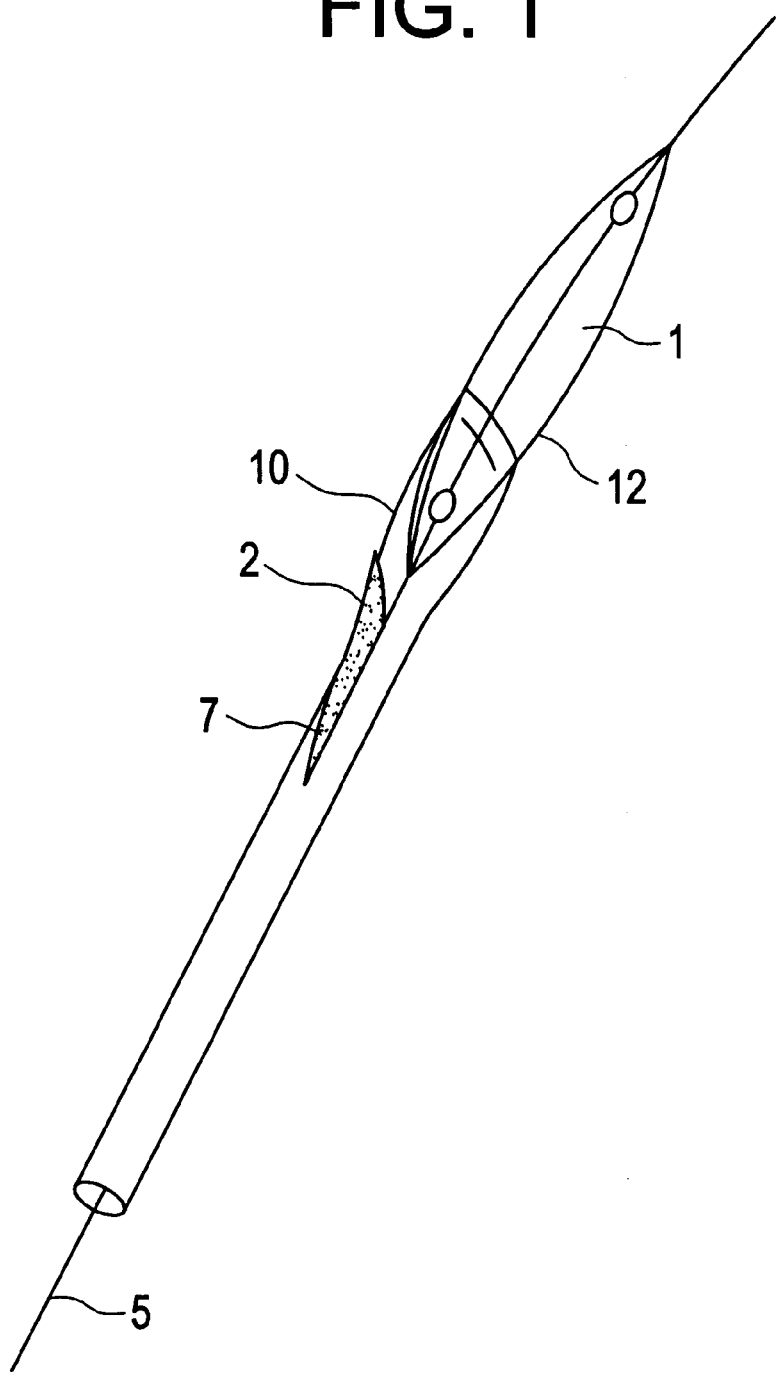
FIG. 1 shows a device during the introduction phase.

As shown in FIG. 1, the device is comprised of an essentially cylindrical balloon (1). This balloon (1) is advantageously inflatable so as to provide the supplementary function of expansion of a stent (12) and to form a lateral asymmetrical extension or projection (2).

It is extended at its distal end by a projection (2). The projection is preferably further provided with a radio-opaque marker (7) as seen in FIGS. 4 and 5. In some embodiments, the projection (2), itself, may be the marker.

During the introduction phase via the endoscopic route, the projection (2) is folded in axial position. It can be maintained by a sheath (10) which maintains the projection (2) in the flat position.

Figure 2:
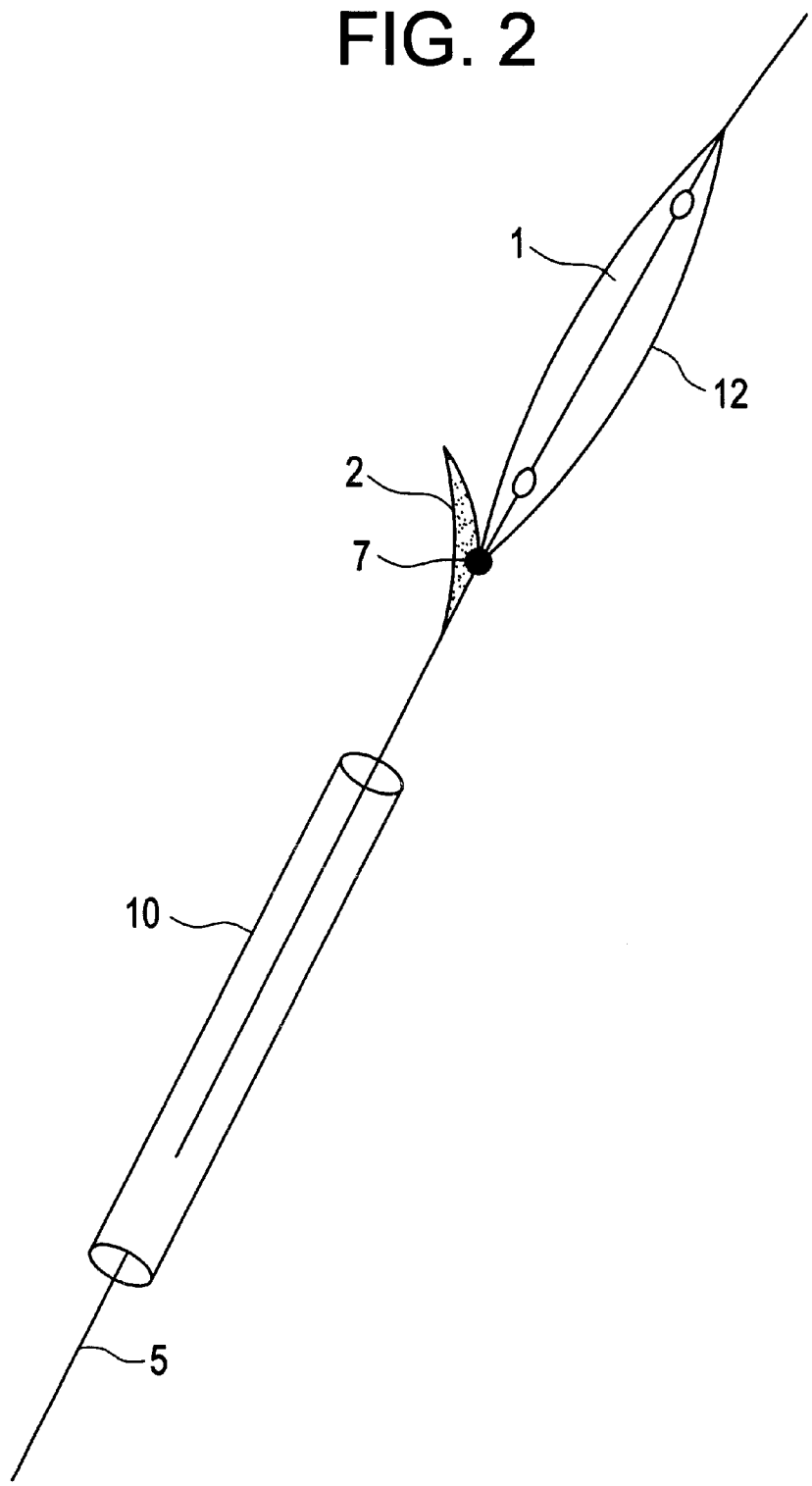
FIG. 2 shows a device during the positioning phase.

This sheath (10) is attached to a thread (5) allowing it to be withdrawn in the proximal direction so as to release the projection (2) as shown in FIG. 2. An asymmetrical radio-opaque marker (7) is preferably provided on the sheath (10).

The projection is then oriented in a radial direction. It constitutes an angular reference point enabling the positioning of the device and the apparatus that it supports, for example, a beveled stent. The projection (2) presents a radio-contrasted reference point (7) enabling verification of the orientation and correct positioning of the beveled stent.

It can also be implemented in the form of a principal balloon in tubular form, extended by a separately inflatable lateral protuberance.

It can also be implemented in the form of a tubular element extended at its distal end by a silicone projection or by an inflatable projection.

The projection can be proximal or distal in relation to the balloon or other stent-carrier systems, if the balloon is self-expandable with shape memory.

FIG. 3 shows a sectional view of an implementation variant with a detachable sleeve (10) in the introduction position and FIGS. 4 and 5 show views of implementation variants after withdrawal of the detachable sleeve.

The catheter (11) forms a support of the beveled stent (12). This catheter (11) has for this purpose a distal part 913) the section of which corresponds to the interior section of the endoprosthesis in the retracted position. A shoulder (14) assures positional locking of the stent (12).

The sleeve (10) can be withdrawn by pulling on a thread attached on the end of said sleeve. Withdrawal of the sleeve (10) releases the lateral projection (2), which can be in the distal position in front off the stent (10) as shown in FIG. 4, or in the proximal position behind the stent (12) as shown in FIG. 5.

FIGS. 6 to 9 show other implementation variants, in which the lateral asymmetrical projection is a metallic guide. The metal guide (20) traverses the carrier catheter

(11) and emerges in the proximal zone via an opening (21) which can be behind the stent (12) as shown in FIGS. 6 and 7 or in front of the stent (12) as shown in FIGS. 8 and 9. The opening (21) is provided in the slanted zone (bevel) of the stent (12) intended for attachment with the daughter branch.

The guide (20) is introduced in the daughter branch of the arterial bifurcation. It can be directed in the antegrade direction or in the retrograde direction depending on the configuration of the channel and its orifice arranged in the catheter (11).

The markers, projections or guide are maintained against the carrier catheter (11) by means of the external sleeve (10) during the step comprising introduction into the artery. The withdrawal of the retractable sleeve (10) causes erection of the projection, and allows the guide (20) to advance. Withdrawal of the sleeve can be implemented on the proximal or distal side.

What is claimed is:

1. A device for positioning an apparatus introduced into an arterial network via an endoscope in a bifurcated vessel having two daughter vessels, only one of which is to be treated, the device comprising:

a tubular element having an asymmetrical lateral extension for angular positioning of the apparatus; and a detachable sleeve which, at the time of the introduction into an artery, surrounds the tubular element and the lateral extension to maintain the lateral extension in a folded position against the tubular element, the detachable sleeve being attached to a thread, wherein the asymmetrical extension can be released by pulling on the thread and by thus withdrawing the sleeve.

2. The device according to claim 1, wherein the tubular element is an inflatable balloon.

3. The device according to claim 1, wherein the tubular element is formed by an inflatable balloon extended by a lateral protuberance as the asymmetrical lateral extension.

4. The device according to claim 3, wherein the balloon is extended by the lateral protuberance which is separately inflatable.

5. The device according to claim 1, further comprising a radio opaque marker on the lateral extension which provides a radio-contrasted reference point.

6. The device according to claim 1, further comprising a retention means for maintaining the lateral extension in a folded position against the tubular element.

7. The device according to claim 6, wherein the retention means can be released by pulling on an attached thread.

8. The device according to claim 1, wherein the detachable sleeve comprises an radio-opaque marker.

9. The device according to claim 1, wherein said apparatus is a stent.

10. A positioning device for use with a stent having a beveled end comprising:

a tubular element and an asymmetrical extension foldably connected to the tubular element, the asymmetrical extension extending laterally outwardly from the tubular element unless held in another position by a retainer; and a retainer for selectively holding and releasing said asymmetrical extension, wherein the retainer is a detachable sleeve extending around the tubular element and the asymmetrical extension.

* * * * *